United States Patent [19]

Fischer, deceased

[11] 3,966,452

[45] June 29, 1976

[54] HERBICIDE MIXTURES OF 3-LOWER ALKYL-2,1,3-BENZOTHIADIAZINONE-(4)-2,2-DIOXIDES OR SALTS THEREOF AND LOWER ALKYL N-(4-AMINOBENZENESULFONYL)-CARBAMATES

[75] Inventor: Adolf Fischer, deceased, lat of Mutterstadt, Germany, by Caecilia Emma Fischer, legal representative

[73] Assignee: BASF Aktiengesellschaft, Ludwigshafen (Rhine), Germany

[22] Filed: Mar. 17, 1975

[21] Appl. No.: 559,322

Related U.S. Application Data

[60] Continuation-in-part of Ser. No. 432,685, Jan. 11, 1974, abandoned, which is a division of Ser. No. 343,629, March 22, 1973, Pat. No. 3,888,655.

[30] Foreign Application Priority Data

Apr. 13, 1972 Germany............................ 2217722

[52] U.S. Cl..................................... 71/91; 71/103
[51] Int. Cl.²........................................... A01N 9/12
[58] Field of Search................................. 71/91, 103

[56] References Cited
UNITED STATES PATENTS 3,708,277 1/1973 Zeidler et al............................. 71/91
3,823,008 7/1974 Carpenter et al....................... 71/103

OTHER PUBLICATIONS

Fischer I, "Herbicidal Compositions," (1971) C.A. 74 No. 110,714w, (1971).

Fischer II, "Herbicidal Compositions, etc.;" (1971) C.A. 75 No. 75217h, (1971).

*Primary Examiner*—Glennon H. Hollrah
*Attorney, Agent, or Firm*—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide or a salt thereof and (b) a compound of the formula

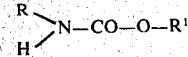

where R denotes aminobenzenesulfonyl and $R^1$ denotes lower alkyl.

3 Claims, No Drawings

HERBICIDE MIXTURES OF 3-LOWER ALKYL-2,1,3-BENZOTHIADIAZINONE-(4)-2,2-DIOXIDES OR SALTS THEREOF AND LOWER ALKYL N-(4-AMINOBENZENESULFONYL)-CARBAMATES

RELATED APPLICATION

This application is a continuation-in-part of application Ser. No. 432,685, filed Jan. 11, 1974, now abandoned which in turn is a division of application Ser. No. 343,629, filed Mar. 22, 1973, now U.S. Pat. No. 3,888,655, the disclosures of which are incorporated herein by reference.

The present invention relates to a herbicide comprising a composition of several active ingredients.

It is known that substituted phenyl ethers, carbamates, terephthalates, acid amides, benzoic acids, fluorenecarboxylic acids and benzothiadiazinones have a herbicidal action. However, this action is poor.

It has been found that a composition of
a. a compound of the formula

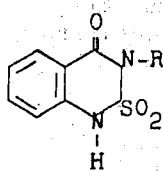

where R denotes lower alkyl of a maximum of 4 carbon atoms, or its salts, such as alkali metal, alkaline earth metal, ammonium, hydroxyalkylammonium, alkylammonium and hydrazine salts, e.g., salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and
b. a compound of the formula

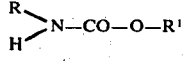

where R denotes aminobenzenesulfonyl and $R^1$ denotes lower alkyl, have a herbicidal action superior to that of their individual components.

Active ingredients (a) to (b) may be applied in amounts of 0.5 to 5 kg per hectare.

The weight ratio of a : b is from 5:1 to 1:5, preferably from 3:1 to 1:3.

The compositions of the invention are suitable for controlling unwanted plants, e.g., dicotyledonous seed weeds, monocotyledonous grassy seed weeds and Cyperaceae in crops such as cereals, rice, soybeans, Indian corn, potatoes, peas, and beans.

The compositions may be used pre- and/or postemergence.

The agents according to the invention may be used as solutions, emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE 1

In the greenhouse, various plants were treated at a growth height of from 1 to 25 cm with the following amounts of the following individual active ingredients and compositions thereof as dispersions, suspensions, emulsions, aqueous solutions or pastes:

I 3-isopropyl-2,1,3-benzothiadiazinone-(4)-2,2-dioxide, 0.5, 0.75, 1 and 1.5 kg/ha;
II 3-isopropyl-2,1,3-benzothiadiazinone-(4)-2,2-dioxide, sodium salt, 0.5, 0.75, 1 and 1.5 kg/ha;
III 3-isopropyl-2,1,3-benzothiadiazinone-(4)-2,2-dioxide, dimethylamine salt, 0.5, 0.75, 1 and 1.5 kg/ha;
IV 3-isopropyl-2,1,3-benzothiadiazinone-(4)-2,2-dioxide, diethanolamine salt, 0.5, 0.75, 1 and 1.5 kg/ha;
V methyl N-(4-aminobenzenesulfonyl)-carbamate, 0.5, 0.75, 1 and 1.5 kg/ha;
I+V, II+V, III+V and IV+V each of these compositions at rates of 0.5+1, 1+0.5 and 0.75+0.75 kg/ha.

After 2 to 3 weeks it was ascertained that the compositions had a better herbicidal action than their components, combined with the same good crop plant compatibility. The results are given below:

| Active ingredient | I | | | | II | | | | III | | | | IV | | | | V | | | |
|---|---|---|---|---|---|---|---|---|---|---|---|---|---|---|---|---|---|---|---|---|
| kg/ha | 0.5 | 0.75 | 1 | 1.5 | 0.5 | 0.75 | 1 | 1.5 | 0.5 | 0.75 | 1 | 1.5 | 0.5 | 0.75 | 1 | 1.5 | 0.5 | 0.75 | 1 | 1.5 |
| Crop plants: | | | | | | | | | | | | | | | | | | | | |
| Saccharum officinarum | 0 | 0 | 0 | 0 | 0 | 0 | 0 | 0 | 0 | 0 | 0 | 0 | 0 | 0 | 0 | 0 | 0 | 0 | 0 | 0 |
| Solanum tuberosum | 0 | 0 | 0 | 0 | 0 | 0 | 0 | 0 | 0 | 0 | 0 | 0 | 0 | 0 | 0 | 0 | 0 | 0 | 0 | 5 |
| Pisum sativum | 0 | 0 | 0 | 0 | 0 | 0 | 0 | 0 | 0 | 0 | 0 | 0 | 0 | 0 | 0 | 0 | 0 | 0 | 0 | 5 |

-continued

| Active ingredient | I | | | | II | | | | III | | | | IV | | | | V | | | |
|---|---|---|---|---|---|---|---|---|---|---|---|---|---|---|---|---|---|---|---|---|
| kg/ha | 0.5 | 0.75 | 1 | 1.5 | 0.5 | 0.75 | 1 | 1.5 | 0.5 | 0.75 | 1 | 1.5 | 0.5 | 0.75 | 1 | 1.5 | 0.5 | 0.75 | 1 | 1.5 |
| Unwanted plants: | | | | | | | | | | | | | | | | | | | | |
| Galium aparine | 30 | 35 | 40 | 60 | 30 | 40 | 45 | 60 | 28 | 40 | 50 | 60 | 35 | 45 | 60 | 67 | 20 | 30 | 36 | 40 |
| Sinapis arvensis | 30 | 45 | 60 | 75 | 25 | 40 | 50 | 75 | 30 | 40 | 55 | 80 | 30 | 42 | 62 | 85 | 30 | 40 | 50 | 60 |
| Avena fatua | 0 | 2 | 5 | 5 | 0 | 0 | 0 | 5 | 0 | 0 | 0 | 0 | 0 | 0 | 0 | 0 | 35 | 45 | 60 | 80 |

| Active ingredient | I + V | | | II + V | | | III + V | | | IV + V | | |
|---|---|---|---|---|---|---|---|---|---|---|---|---|
| kg/ha | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 | 0.5 / 1 | 1 / 0.5 | 0.75 / 0.75 |
| Crop plants: | | | | | | | | | | | | |
| Saccharum officinarum | 0 | 0 | 0 | 0 | 0 | 0 | 0 | 0 | 0 | 0 | 0 | 0 |
| Solanum tuberosum | 0 | 0 | 0 | 0 | 0 | 0 | 0 | 0 | 0 | 0 | 0 | 0 |
| Pisum sativum | 0 | 0 | 0 | 0 | 0 | 0 | 0 | 0 | 0 | 0 | 0 | 0 |
| Unwanted plants: | | | | | | | | | | | | |
| Galium aparine | 100 | 100 | 100 | 100 | 100 | 100 | 100 | 100 | 100 | 100 | 100 | 100 |
| Sinapis arvensis | 100 | 100 | 100 | 100 | 100 | 100 | 100 | 100 | 100 | 100 | 100 | 100 |
| Avena fatua | 95 | 80 | 86 | 98 | 82 | 90 | 96 | 80 | 93 | 100 | 82 | 90 |

0 = no damage
100 = complete destruction

EXAMPLE 2

In the greenhouse, various plants were treated at a growth height of from 1 to 25cm with the following amounts of the following individual active ingredients and compositions thereof as dispersions, suspensions, emulsions, aqueous solutions or pastes:

I 3-isopropyl-2,1,3-benzothiadiazinone-(4)-2,2-dioxide

II 3-isopropyl-2,1,3-benzothiadiazinone-(4)-2,2-dioxide, sodium salt

III 3-isopropyl-2,1,3-benzothiadiazinone-(4)-2,2-dioxide, dimethylamine salt

IV 3-isopropyl-2,1,3-benzothiadiazinone-(4)-2,2-dioxide, diethanolamine salt

V methyl N-(4-aminobenzenesulfonyl)-carbamate each of these compounds at rates of 0.5, 1, 1.5, 2, 2.5 and 3 kg/ha;

I + V, II + V, III + V and IV + V, each at rates of 0.5 + 1.5, 1.5 + 0.5, 1 + 1, 1.5 + 1.5, 2.5 + 0.5 and 0.5 + 2.5 kg/ha.

After 2 to 3 weeks it was ascertained that the compositions had a better herbicidal action than their components, combined with the same crop plant compatibility.

The results are given below:

| Active ingredient | I | | | | | | II | | | | | | III | | | | | |
|---|---|---|---|---|---|---|---|---|---|---|---|---|---|---|---|---|---|---|
| kg/ha | 0.5 | 1 | 1.5 | 2 | 2.5 | 3 | 0.5 | 1 | 1.5 | 2 | 2.5 | 3 | 0.5 | 1 | 1.5 | 2 | 2.5 | 3 |
| Crop plants: | | | | | | | | | | | | | | | | | | |
| Saccharum officinarum | 0 | 0 | 0 | 0 | 0 | 0 | 0 | 0 | 0 | 0 | 0 | 0 | 0 | 0 | 0 | 0 | 0 | 0 |
| Solanum tuberosum | 0 | 0 | 0 | 0 | 0 | 0 | 0 | 0 | 0 | 0 | 0 | 0 | 0 | 0 | 0 | 0 | 0 | 0 |
| Pisum Sativum | 0 | 0 | 0 | 0 | 0 | 0 | 0 | 0 | 0 | 0 | 0 | 0 | 0 | 0 | 0 | 0 | 0 | 0 |
| Unwanted plants: | | | | | | | | | | | | | | | | | | |
| Galium aparine | 30 | 40 | 60 | 75 | 90 | 95 | 30 | 45 | 60 | 80 | 90 | 94 | 28 | 50 | 60 | 75 | 90 | 95 |
| Avena fatua | 0 | 5 | 5 | 7 | 9 | 10 | 0 | 0 | 5 | 7 | 10 | 10 | 0 | 0 | 0 | 3 | 6 | 10 |

| Active ingredient | IV | | | | | | V | | | | | |
|---|---|---|---|---|---|---|---|---|---|---|---|---|
| kg/ha | 0.5 | 1 | 1.5 | 2 | 2.5 | 3 | 0.5 | 1 | 1.5 | 2 | 2.5 | 3 |
| Crop plants: | | | | | | | | | | | | |
| Saccharum officinarum | 0 | 0 | 0 | 0 | 0 | 0 | 0 | 0 | 0 | 5 | 10 | |
| Solanum tuberosum | 0 | 0 | 0 | 0 | 0 | 0 | 0 | 0 | 5 | 7 | 10 | 15 |
| Pisum sativum | 0 | 0 | 0 | 0 | 0 | 0 | 0 | 0 | 5 | 10 | 15 | 17 |
| Unwanted plants: | | | | | | | | | | | | |
| Galium aparine | 35 | 60 | 67 | 80 | 90 | 95 | 20 | 36 | 40 | 60 | 75 | 85 |
| Avena fatua | 0 | 0 | 0 | 2 | 5 | 10 | 35 | 60 | 80 | 85 | 90 | 100 |

| Active ingredient | I + V | | | | | | II + V | | | | | |
|---|---|---|---|---|---|---|---|---|---|---|---|---|
| kg/ha | 0.5 / 1.5 | 1.5 / 0.5 | 1 / 1 | 1.5 / 1.5 | 2.5 / 0.5 | 0.5 / 2.5 | 0.5 / 1.5 | 1.5 / 0.5 | 1 / 1 | 1.5 / 1.5 | | |
| Crop plants: | | | | | | | | | | | | |
| Saccharum officinarum | 0 | 0 | 0 | 0 | 0 | 5 | 0 | 0 | 0 | 0 | | |
| Solanum tuberosum | 5 | 0 | 0 | 0 | 0 | 10 | 5 | 0 | 0 | 5 | | |
| Pisum sativum | 5 | 0 | 0 | 5 | 0 | 15 | 5 | 0 | 0 | 5 | | |
| Unwanted plants: | | | | | | | | | | | | |
| Galium aparine | 100 | 100 | 100 | 100 | 100 | 100 | 100 | 100 | 100 | 100 | | |
| Avena fatua | 100 | 85 | 100 | 100 | 100 | 100 | 100 | 87 | 100 | 100 | | |

| Active ingredient | II + V | | | | III + V | | | | IV + V | | | | | |
|---|---|---|---|---|---|---|---|---|---|---|---|---|---|---|
| kg/ha | 2.5 / 0.5 | 0.5 / 2.5 | 0.5 / 1.5 | 1.5 / 0.5 | 1 / 1 | 1.5 / 1.5 | 2.5 / 0.5 | 0.5 / 2.5 | 0.5 / 1.5 | 1.5 / 0.5 | 1 / 1 | 1.5 / 1.5 | 2.5 / 0.5 | 0.5 / 2.5 |
| crop plants: | | | | | | | | | | | | | | |
| Saccharum officinarum | 0 | 5 | 0 | 0 | 0 | 0 | 0 | 5 | 0 | 0 | 0 | 0 | 0 | 5 |
| Solanum tuberosum | 0 | 10 | 5 | 0 | 0 | 5 | 0 | 10 | 5 | 0 | 0 | 5 | 0 | 10 |
| Pisum sativum | 0 | 15 | 5 | 0 | 0 | 5 | 0 | 15 | 5 | 0 | 0 | 5 | 0 | 15 |
| Unwanted plants: | | | | | | | | | | | | | | |
| Galium oparine | 100 | 100 | 100 | 100 | 100 | 100 | 100 | 100 | 100 | 100 | 100 | 100 | 100 | 100 |
| Avena fatua | 90 | 100 | 100 | 85 | 100 | 100 | 90 | 100 | 100 | 85 | 100 | 100 | 90 | 100 |

0 = no damage
100 = complete destruction

It is claimed:

1. A herbicide composition comprising an inert carrier having dispersed therein a herbicidally effective amount of a mixture of herbicides consisting essentially of a. a compound of the formula

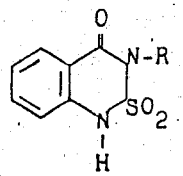

where R denotes lower alkyl of a maximum of 4 carbon atoms, or an alkali metal, alkaline earth metal, ammonium, lower alkylammonium, lower hydroxyalkylammonium or hydrazine salt thereof, and b. a compound of the formula

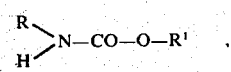

where R denotes aminobenzenesulfonyl and $R^1$ denotes lower alkyl in a weight ratio of a:b of 3:1 to 1:3.

2. A composition as claimed in claim 1, wherein R in compound (a) is isopropyl.

3. A composition as claimed in claim 1, wherein R in compound (a) is isopropyl, and compound (b) is methyl-N-(4-aminobenzenesulfonyl)-carbamate.

* * * * *